United States Patent
Flohé et al.

(10) Patent No.: US 6,291,217 B1
(45) Date of Patent: Sep. 18, 2001

(54) GLUTATHIONYLSPERMIDINE SYNTHETASE AND PROCESSES FOR RECOVERY AND USE THEREOF

(75) Inventors: Leopold Flohé, Mascheroder Weg 1, Braunschweig D-38124 (DE); Kerstin Koenig; Ulrich Menge, both of Braunschweig (DE)

(73) Assignee: Leopold Flohe (DE)

( * ) Notice: Subject to any disclaimer, the term of this patent is extended or adjusted under 35 U.S.C. 154(b) by 0 days.

(21) Appl. No.: 09/330,740

(22) Filed: Jun. 11, 1999

Related U.S. Application Data

(63) Continuation of application No. PCT/EP97/06982, filed on Dec. 12, 1997.

(30) Foreign Application Priority Data

Dec. 12, 1996 (EP) ................................................. 96120014

(51) Int. Cl.[7] ..................................................... C12N 9/00
(52) U.S. Cl. ......................... 435/183; 435/188; 435/243; 435/258.1; 435/258.3; 435/947; 530/350; 536/23.2
(58) Field of Search ........................... 530/350; 435/69.2, 435/7.22, 184, 188, 243, 258.1, 258.3, 947, 183; 424/146.1; 536/23.2

(56) References Cited

PUBLICATIONS

"Biosynthesis of The Trypanosomatid Metabolite Trypanothione: Purification and Characterization of Trypanothione Synthetase from *Crithidia fasciculata*", Henderson et al., XP–002065393 Biochemistry 1990, pp. 3924–3929.

"Purification of Glutathionylspermidine and Trypanothione Synthetases from *Crithidia fasciculata*", Smith et al., XP–002065394, Protein Science 1992, pp. 874–883.

"Phosphonic Acid and Phosphinic Acid Tripeptides as Inhibitors of Glutathionylspermidine Synthetase", Verbruggen et al., XP–002065395, Bioorganic & Medicinal Chemistry Letters, vol. 6, No. 3, 1996, pp. 253–258.

"Convenient Isolation and Kinetic Mechanism of Glutathionylspermidine Synthetase from *Crithidia fasciculata*", Koenig et al., The Journal of Biological Chemistry, vol. 272, No. 18, May 2, 1997, pp. 11908–11915.

"Cloning and Characterization of the Trypanothione Synthetase Gene From *Crithidia fasciculata*", Tetaud et al., XP–002065397, Unpublished, Apr. 6, 1998.

International Search Report in PCT/EP97/06982, dated Jun. 5, 1998.

Tetraud et al. Cloning and characterization of the two enzymes responsible for trypanothione biosynthesis in *Crithidia fasciculata*. The Journal of Biological Chemistry. vol. 273, No. 31 (1998) pp. 19383–19390.*

* cited by examiner

*Primary Examiner*—Jeffrey Stucker
*Assistant Examiner*—Ulrike Winkler
(74) *Attorney, Agent, or Firm*—Marshall, O'Toole, Gerstein, Murray & Borun

(57) ABSTRACT

The present invention describes an enzyme showing glutathionylspermidine synthetase-activity and being distinct from known enzymes with similar activities in several physicochemical parameters, a novel process to isolate said enzyme from *Crithidia fasciculata*, tools for the production thereof in genetically transformed organisms, and its use as a molecular target for the discovery of trypanocidal drugs.

11 Claims, 15 Drawing Sheets

Fig. 1

Figure 3A:
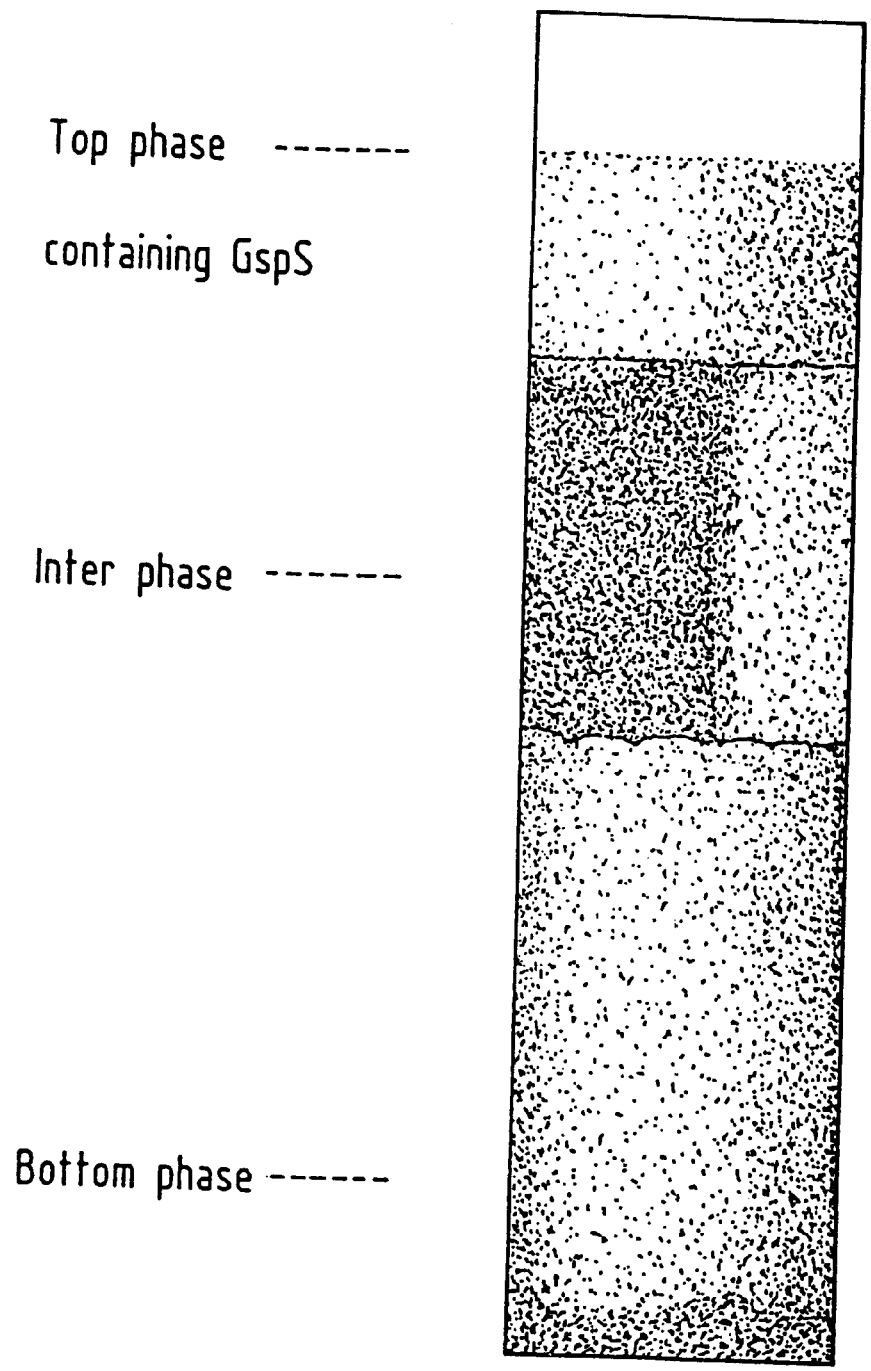

SEQ ID NO 1
(10) V P F G E V Q G Y A P G H I P A Y S N K (29)
     + * * *   + * * * * *   +   + * *

SEQ ID NO 2
(133) S I I T G L D S P F A A I (145)
      * * *   *       +     *

SEQ ID NO 3
(191) T Y E P T E (196)
        *   * *

SEQ ID NO 4
(202) N E I P R P L T H K (211)
      * *     *       +

SEQ ID NO 5
(227) L D L N D P A E (234)
      * *   * * + +

SEQ ID NO 6
(500) I L P I I Y H N H P D H P A I L R A E (518)
      * * * * + +       *   *     + *     +

SEQ ID NO 7
(535) I V G R V G R N V T I T D G (548)
        * + * *   *   *   + . +

```
SEQ ID NO 9   9              18            27            36            45            54
5' TAC AGC AAC AAG CAC GAT CAC TTC TTC TCG GGT GAG CGC AGC ATT GAC GAT AAC
   --- --- --- --- --- --- --- --- --- --- --- --- --- --- --- --- --- ---
    Y   S   N   K   H   D   H   F   F   S   G   E   R   S   I   D   D   N

SEQ ID NO 8  63            72            81            90            99           108
   GTC TTC TGC GGC TTC AAG TAC CAG TGC GTC GAG TTC GCG CGC TGG CTG TTG
   --- --- --- --- --- --- --- --- --- --- --- --- --- --- --- --- ---
    V   F   C   G   F   K   Y   Q   C   V   E   F   A   R   W   L   L 117           126           135           144           153           162
   GAG CGG AAG GGG CTG GTG CTG CCG GAC GTG AAT TGG GCG TGC CAC ATC TTC AAG
   --- --- --- --- --- --- --- --- --- --- --- --- --- --- --- --- --- ---
    E   R   K   G   L   V   L   P   D   V   N   W   A   C   H   I   F   K 171           180           189           198           207           216
   CTC AAG AGC GTG AAG GAT GCC GCG ACG GCG GAG GAG GTG CCG GTG ATC GCC GTG
   --- --- --- --- --- --- --- --- --- --- --- --- --- --- --- --- --- ---
    L   K   S   V   K   D   A   A   T   A   E   E   V   P   V   I   A   V
```

FIGURE 2A

```
      225         234         243         252         261         270
CGC AAC GGC ACG GAG GCG AAG CCG GAG CCC GAC ACG CTG ATC ATC TAC CCC TCG
 R   N   G   T   E   A   K   P   E   P   D   T   L   I   I   Y   P   S 279         288         297         306         315         324
TCG GAC GTC AAC ACC GTG GGC CAC GTC GGC GCC ATC ACG GAG GTC GGC GAC GAC
 S   D   V   N   T   V   G   H   V   G   A   I   T   E   V   G   D   D 333         342         351         360         369         378
TAC GTG TGC ATT GCG GAC CAG AAC TAC CGC TTT CAC AAG TGG GAG GCG TCC TAC
 Y   V   C   I   A   D   Q   N   Y   R   F   H   K   W   E   A   S   Y 387         396         405         414         423         432
TCC TAC AAG TTG AAG CTG CAG CAC AAG GAT GGG GTT TGG ACG ATC ATC GAC GAC
 S   Y   K   L   K   L   Q   H   K   D   G   V   W   T   I   I   D   D 441         450         459         468         477         486
ATC GAC CCC AAC GAT GTC GAG ATT CCG CTT GGC TGG GTG ACC TTC CCC GGC TAC
                                                                    A
 I   D   P   N   D   V   E   I   P   L   G   W   V   T   F   P   G   Y
```

FIGURE 2B

```
             495             504             513             522             531             540
        GAG AAC CGG CCG GAA GGC GCC GCG CCA CCG GCG CTG CAC CCC TCT CTC CAC TTC
          A
        --- --- --- --- --- --- --- --- --- --- --- --- --- --- --- --- --- ---
         E   N   R   P   E   G   A   A   P   P   A   L   H   P   S   L   H   F 549             558             567             576             585             594
        CAG CCC CCG GAG GAG CCG TAC CTG GTC CGC AAG ACG TAC GAG CCG ACG GAG ACG
              G               A                    T
        --- --- --- --- --- --- --- --- --- --- --- --- --- --- --- --- --- ---
         Q   P   P   E   E   P   Y   L   V   R   K   T   Y   E   P   T   E   T
                                                    N 603             612             621             630             639             648
        AAG GCG AAC TGG CTG GAT TTG AAC GAC CCC GCA GAG AAG CTC TTT GTG GAG GAG
                                              T   T
        --- --- --- --- --- --- --- --- --- --- --- --- --- --- --- --- --- ---
         K   A   N   W   L   D   L   N   D   P   A   E   K   L   F   V   E   E 657             666             675             684             693             702
        TTC GGC ATG GAC GTC AGC CGC TCC CGC CTC GAG ACG ACG GAG ACG GTG AAC TAC TAC
                                                      C
        --- --- --- --- --- --- --- --- --- --- --- --- --- --- --- --- --- ---
         F   G   M   D   V   S   R   S   R   L   E   E   T   T   V   N   Y   Y
```

FIGURE 2C

```
GAG TGC GAC CAT GAG TTC CAC CTC CGC TGC ATC GCC TAC GGG ACG CAG CTG CAC
 E   C   D   H   E   F   H   L   R   C   I   A   Y   G   T   Q   L   H

GAC TAC TTC ATG GAG GCC ACC GCG CAG GTC ATC AAC GAG CGG CTC CGC ATC
 D   Y   F   M   E   A   T   A   Q   V   I   N   D   E   R   L   R   I

TTT AAG ATT CCA GAG GAG CTG TGG CCC CGC ATG CGC CAC TCC TGG AAG TAC CAG
 F   K   I   P   E   E   L   W   P   R   M   R   H   S   W   K   Y   Q

CAG ACG TAC ATC TCT GGC CGC TTT GAC TTC GCC TAC AAC AAC GAG ACG CAC CAG
 Q   T   Y   I   S   G   R   F   D   F   A   Y   N   N   E   T   H   Q
                                                      A

ATG AAG TGC TTC GAG TAC AAC GCC GAC AGC GCG TCG ACG CTG GAG TGC GGC
                     A                                  A
 M   K   C   F   E   Y   N   A   D   S   A   S   T   L   E   C   G
```

FIGURE 2D

```
     981            990           999          1008          1017          1026
CGC ATT CAG CAG AAG TGG GCC GAG TCG GCG GGG CTG GAC AAG GAG GGC ACG CGC
         C   A
 R   I   Q   Q   K   W   A   E   S   A   G   L   D   K   E   G   T   R 1035           1044          1053         1062          1071          1080
GGC TCC GGC TGG GCC GTC GAG CGC AAC CTG CCG ACC GCG TGG GCC ACC TGC GGC
 G   S   G   W   A   V   E   R   N   L   P   T   A   W   A   T   C   G 1089           1098          1107         1116          1125          1134
GCC ACT GGT CGC CAC TTC CTC GTG GAC GAT GAG AAG GAG CAG GAG TAC ACG
 A   T   G   R   H   F   L   V   D   D   E   K   E   E   Q   E   Y   T 1143           1152          1161         1170          1179          1188
GCC CTT TAC TGC CTG CAG GCG CGG AAG CGT GGG CTG GAG GGG AAG CTG TGC GTC
 A   L   Y   C   L   Q   A   R   K   R   G   L   E   G   K   L   C   V 1197           1206          1215         1224          1233          1242
ATG TAC GAC GAG TTC CGC TTC AAC GAG GAG GGC TAC GTC GTG GAC AGC GAT GGG
 M   Y   D   E   F   R   F   N   E   E   G   Y   V   V   D   S   D   G
```

FIGURE 2E

```
      1251           1260           1269           1278           1287           1296
GTG CGG GTG CGC AAC ATT TGG AAG ACG TGG ATG ACG GAG TCG GCC ATC AGC GAC
 V   R   V   R   N   I   W   K   T   W   M   W   E   S   A   I   S   D 1305           1314           1323           1332           1341           1350
TAC TTC GCC GCG CAG GCC GAG CGC GTG CGA CTG GAA GGC GAC GCC GCC GAC AAG
 Y   F   A   A   Q   A   E   R   V   R   L   E   G   D   A   A   D   K 1359           1368           1377           1386           1395           1404
GTG CGG CTC TGT GAC CTG ATG CTC GGC AAG GAC TGG GTC ATC TTG TAC TTT GAG
                                                 A
 V   R   L   C   D   L   M   L   G   K   D   W   V   I   L   Y   F   E
                                                 D 1413           1422           1431           1440           1449           1458
CCG ATG TGG AAG CTG ATC CCG AGC AAC AAG GTC ATC CTG CCC ATC ATC TAC CAC
                                         G
 P   M   W   K   L   I   P   S   N   K   V   I   L   P   I   I   Y   H
                                         G 1467           1476           1485           1494           1503           1512
AAC CAC CCT GAT CAC CCG GCG ATC CTG CGC GCT CTG GAG TAC GAG CTC ACC GAC GAG
 N   H   P   D   H   P   A   I   L   R   A   L   E   Y   E   L   T   D   E
```

FIGURE 2F

```
           1521           1530              1539              1548              1557           1566
      CTC CTA CGC TGT GGC TAC GCC AGG AAG CCG ATT GTT TGC CGT GTC GGC CGC AAC ---
       L   L   R   C   G   Y   A   R   K   P   I   V   C   R   V   G   R   N 1575           1584              1593              1602              1611           1620
      GTC ACC ATC ACC GAC GGT GAG ACG GGT GAG GTG CAC GCC GAG TCG GGC GGC AAC TTC ---
       V   T   I   T   D   G   E   T   G   E   V   H   A   E   S   G   G   N   F 1629           1638              1647              1656              1665           1674
      GGC GAG CGG GAT ATG ATT TAC CAG GAG CTC TTC TCC CTG ACG AAG CAG GAT GGT ---
       G   E   R   D   M   I   Y   Q   E   L   F   S   L   T   K   Q   D   G 1683           1692              1701              1710              1719
      TAT TAC GCG ATC ATC GGC GGC ATG CTG GGC GAC GCG TTC AGC GGC 3'
       Y   Y   A   I   I   G   G   M   L   G   D   A   F   S   G
```

FIGURE 2G

| | 1 | 2 | 3 | 4 | 5 | 6 | 7 | 8 | 9 | 10 | 11 | 12 |
|---|---|---|---|---|---|---|---|---|---|---|---|---|
| ATP [mM]:→ | | 0.2 mM | 0.2 mM | 0.5 mM | 0.5 mM | 1 mM | 1 mM | 2 mM | 2 mM | 5 mM | 5 mM | |
| A | blank | 10 | 10 | 10 | 10 | 10 | 10 | 10 | 10 | 10 | 10 | |
| B | blank | 5 | 5 | 5 | 5 | 5 | 5 | 5 | 5 | 5 | 5 | |
| C | blank | 2 | 2 | 2 | 2 | 2 | 2 | 2 | 2 | 2 | 2 | |
| D | blank | 1 | 1 | 1 | 1 | 1 | 1 | 1 | 1 | 1 | 1 | |
| E | | 0.5 | 0.5 | 0.5 | 0.5 | 0.5 | 0.5 | 0.5 | 0.5 | 0.5 | 0.5 | |
| F | | 0.2 | 0.2 | 0.2 | 0.2 | 0.2 | 0.2 | 0.2 | 0.2 | 0.2 | 0.2 | |
| G | | 0.1 | 0.1 | 0.1 | 0.1 | 0.1 | 0.1 | 0.1 | 0.1 | 0.1 | 0.1 | |
| H | | 0 | 0 | 0 | 0 | 0 | 0 | 0 | 0 | 0 | 0 | |

FIGURE 9A

GLUTATHIONYLSPERMIDINE SYNTHETASE AND PROCESSES FOR RECOVERY AND USE THEREOF

This is a continuation of International Application No. PCT/EP97/06982 filed Dec. 12, 1997, the entire disclosure of which is incorporated herein by reference.

Glutathionylspermidine synthetase (GspS) catalyzes the first of two steps of trypanothione biosynthesis, the synthesis of glutathionylspermidine (Gsp) from glutathione (GSH) and spermidine with the consumption of ATP (1). Trypanothione ($N^1$, $N^8$-bis(glutatlhionyl)spermidine, TSH) is a metabolite unique to trypanosomatids such as Trypanosoma species, Leishmania species, and Crithidia fasciculata (2). These parasites comprise pathogens causing widespread and difficult-to-treat tropical diseases such as African sleeping sickness (T. brucei gambiense or T. brucei rhodesiense), Chagas disease (T. cruzi), kala azar (L. donovani), oriental sore (L. tropica) and mucocutaneous leishmaniasis (L. braziliensis). Others (e.g. T. congolense) affect domestic animals, whereas C. fasciculata is pathogenic to insects only.

Since the discovery of TSH in 1985 (3, 4), the pathways for its synthesis and utilization have attracted considerable interest as potential targets for selective therapeutic intervention (5, 6). In all trypanosomatids TSH substitutes for GSH in the defense against hydroperoxides and derived reactive oxygen species because of its ability to reduce peroxides either enzymatically (7–9) or spontaneously (10). It thereby protects the parasitic trypanosomatids, which apparently are deficient in catalase and glutathione peroxidases (11), against oxidative stress for instance during host-defense reactions (9, 12, 13). Trypanothione disulfide thereby formed is reduced by the NADPH-dependent trypanothione reductase (14, 15), a flavoprotein homologous to glutathione reductase which together with glutathione peroxidases (16, 17) constitutes a major part of the defense system of the host (18, 19). The precursor of TSH, Gsp, may have a distinct biological role. It was first identified in Escherichia coli (20), where it remains unprocessed to TSH due to the apparent lack of TSH synthetase. In E. coli GspS, and consequently Gsp, is prominent in the stationary phase (20, 21). Similarly, in C. fasciculata Gsp increases substantially during the transition of growth phase to stationary phase, while TSH simultaneously drops (22). These fluctuations of GSH conjugates or the associated variations in cellular spermidine levels have tentatively been implicated in growth regulation (2, 20, 21). The major biological function of TSH in trypanosomatids is to serve as a reducing substrate for thioredoxin-like proteins called tryparedoxins (23). Tryparedoxins in turn may have a variety of functions in replacing thioredoxin which so far could never be identified in trypanosomatids. A prominent role of tryparedoxin consists in the regeneration of tryparedoxin peroxidase after reaction thereof with a hydroperoxide such as $H_2O_2$, a fatty acid hydroperoxide, or a hydroperoxide of a complete lipid (24). Thereby, GspS together with trypanothione synthetase, trypanothione reductase, tryparedoxin, and tryparedoxin peroxidase constitutes the most complex system to protect trypanosomatids against oxidative damage. By analogy, reduced tryparedoxin may also substitue for thioredoxin in other pathways, e.g. in the reduction of ribonucleotides thereby becoming essential for the entire nucleic acid metabolism in trypanosomatids. The first enzyme catalyzing synthesis of Gsp has once been isolated in trace amounts from C. fasciculata (0.5 mg from 500 g wet cell mass) and characterized in terms of the apparent MW, kinetic parameters, and substrate specificity (1).

Another deduced amino acid sequence obtained from C. fasciculata first claimed to represent a trypanothione-synthetase-like protein(acc. number U66520) was submitted to Genbank on Aug. 9, 1996, became available to the public in February 1997 and wvas reported to be the sequence of glutathionylspermidine synthetase without, however, providing any experimental data supporting this assignment. In terms of size and sequence, this putative (GspS of C. fasciculata is not identical with the GspS of C. fasciculata described in the present invention. This protein differs substantially from GspS described here in molecular mass (90 (1) versus 78–79 kDa, respectively) and pH optimum (6.5 (1) versus 7.5). Also, the previously described enzyme reportedly hydrolyzed ATP in the absence of spermidine (1), whereas such activity was not detectable in GspS as characterized here. Taken together, these discrepancies demonstrate that the two preparations can not be considered identical or equivalent.

An enzyme catalyzing the analogous reaction in E. coli has recently been cloned. Surprisingly, this GspS also exhibits a substantial amidase activity with Gsp as substrate. The simultaneous catalysis of Gsp synthesis and breakdown results in an apparently futile ATP consumption, the biological role of which remains speculative (25, 26). Since E. coli does not produce TSH, its GspS has obviously to be seen in a biological context distinct from trypanosomal TSH metabolism, and also the structural and phylogenetic relationship of bacterial and trypanosomal GspS remains to be investigated.

Most importantly, we here describe a method for purification of GspS from C. fasciculata yielding an enzyme pur enough to be sequenced. The partial amino acid sequence enables the identification of the pertinent gene and the heterologous expression therof by methods known per se, thereby making GspS available for the identification of specific inhibitors useful as trypanocidal drugs. Further, we have invented a simple and convenient method to partially purify GspS from C. fasciculata. Such preparation does not catalyze any ATP hydrolysis in the absence of further GspS substrates and cofactors, i. e. spermidine and magnesium. This implies that GspS activity and inhibition thereof can be specifically measured simply by liberation of inorganic phosphate from ATP in such partially purified GspS. This test system is easily automatized for large scale inhibitor screening.

Thus, one embodiment of the invention concerns a protein characterized by its ability to catalyze the synthesis of glutathionylspermidine with a pH optimum of about 7.5.

The protein according to the invention is further characterized by an apparent molecular weight of 78,000±3000 Da.

The protein is further characterized by comprising partial sequences shown in FIG. 1 and being homologous to glutathionylspermidine synthetase/amidase of Escherichia coli. The protein according to the invention is further characterized by being isolated from a species of the family trypanosomatidae or produced in any other species by recombinant DNA techniques making use of the partial amino acid sequences shown in FIG. 1, genetic probes or primers derived thereof or encoding nucleic acid sequences thus obtained, e. g. SEQ ID NO1 (depicted in FIG. 2A through FIG. 2G) or any useful part thereof.

The protein according to the invention is further characterized by comprising the partial amino acid sequence deduced from the nucleic acid sequence SEQ ID NO1.

The protein according to the invention is further characterized by comprising or having a sequence which is at least 70%, preferntially 75% identical to that deduced from SEQ ID NO1, respectively.

The protein according to the invention is also any modification thereof genetically designed for facilitaded purification such as e. g. an carboxyterminal polyhistidine extension.

Another embodiment of the invention is a simple process to purify GspS to an extent that its activity as well as the inhibition thereof can be conveniently but specifically tested by liberation of inorganic phosphate from adenosyltriphosphate (ATP) in the presence of spermidine, glutathione and magnesium ions.

The process of the invention is characterized by making use of aqueous two phase systems containing polyethyleneglycol.

Another embodiment of the invention is the specific determinateion of GspS activity by means of the detection of inorganic phosphate from ATP by partially purified GspS.

This analytical process is characterized by not being disturbed by any other ATP hydrolyzing activity enhanced by glutathionie and spermidinie.

Finally, another embodiment of the invention concerns a pharmaceutical preparation having trypanocidal activity and comprising an inhibitory substance according to the invention or of a protein which can be obtained according to the process according to the invention to produce said protein.

The pharmaceutical composition according to the invention can be characterized in that it can be obtained by use according to the invention and/or by using a test system according to the invention.

The invention is nown described by means of figures and examples

FIG. 1. Partial sequences of GspS from *C. fasciculata* compared to Gsp synthetase/amidas from *Escherichia coli*. The amino acid numbering corresponds to the *E. coli* sequence (23). *=identical amino acids, +=similar amino acids found in GspS from *E. coli*.

FIG. 2A through FIG. 2G. Partial DNA sequence encoding GspS of *C. fasciculata*. Corresponding peptide sequences in the deduced amino acid sequence, which are verified by peptide sequencing of authentic GspS from *C. fasciculata* are underlined.

Figure 3B:
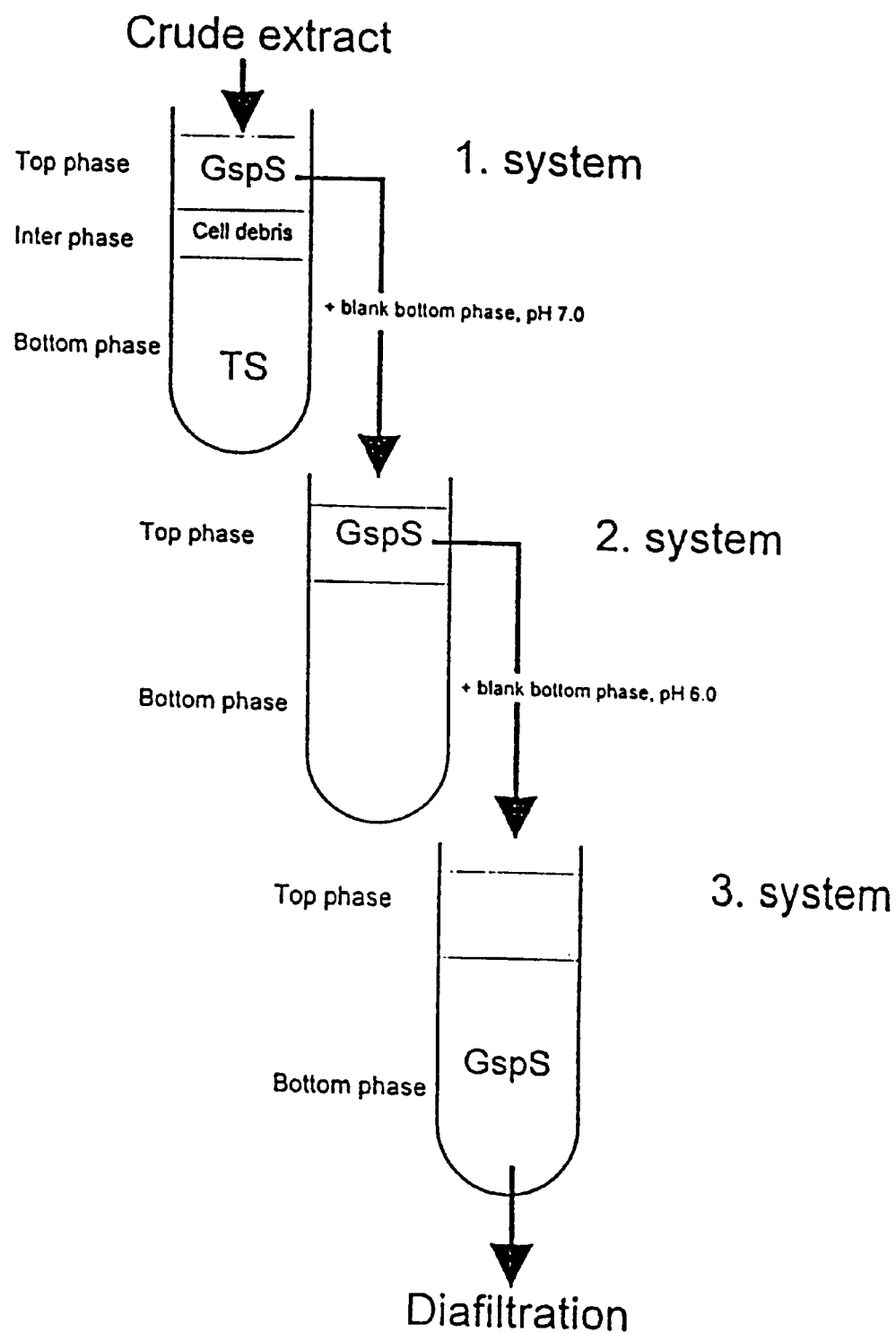

FIG. 3. Extraction of glutathionylspermidine synthetase in aqueous two-phase systems. GspS= glutathionylspermidine synthetase, TS=trypanothione synthetase. For extraction of GspS aqueous two-phase systems were prepared by weighing in concentrated solutions of the phase components and finally the crude extract. A poly (ethylene glycol) (PEG)/phosphate system containing 7.5% (w/w) $PEG_{6000}$, 13% (w/w) Na—K-phosphate, pH 7.0, and 40% crude homogenate. The mixture was gently shaken for 10 min at room temperature and separated by centrifugation at 5000 g.

With the first system we yielded an extraction of GspS into the top phase with a purification factor of 30 in one step.

1. System: GspS was extracted into the top phase of an aqueous two-phase system containing 7.5% (w/w) $PEG_{6000}$ and 13% (w/w) Na—K-phosphate, pH 7.0. 2. System: the PEG-rich top phase of the first system containing GspS was applied to a bottom phase of an identical system containing water instead of cell lysate. 3. System: the top phase of the second phase system was added to an acidified bottom phase of a blank system. The GspS was now extracted into the phosphate-rich bottom phase.

Figure 4:
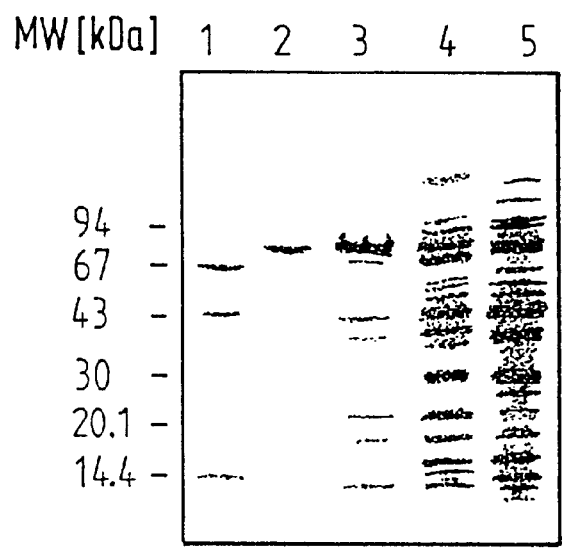

FIG. 4. SDS-PAGE analysis of the glutathionyispermidine synthetase fractions during purification. Lanes are as follows: 1, SDS marker proteins; 2, pooled fractions after chromatography on Mono P; 3, pooled fractions after chromatography on Poros 20 PE; 4, pooled fractions after chromatography on Poros 20 Pi; 5, pooled fractions after chromatography on Resource Q.

Figure 5:
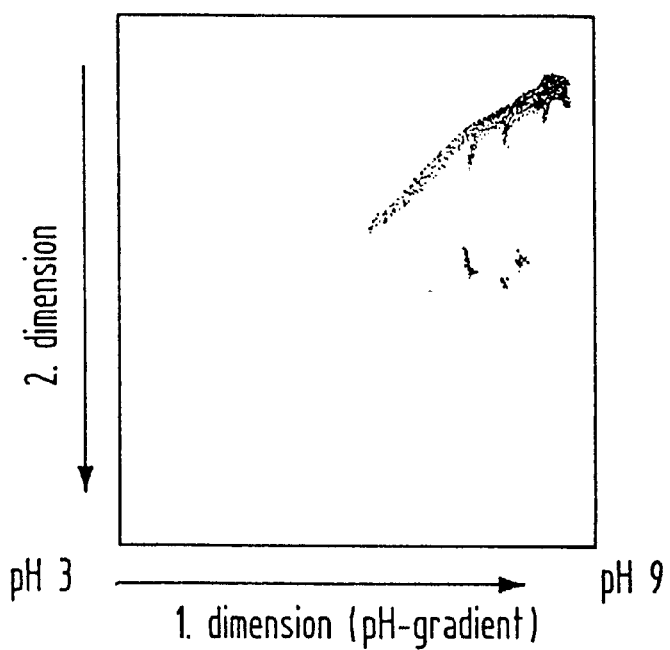

FIG. 5. Titration curve analysis of the homogeneous glutathionylspermidine synthetase. First dimension: isoelectric focusing, run without protein sample; second dimension: native PAGE.

Figure 6:
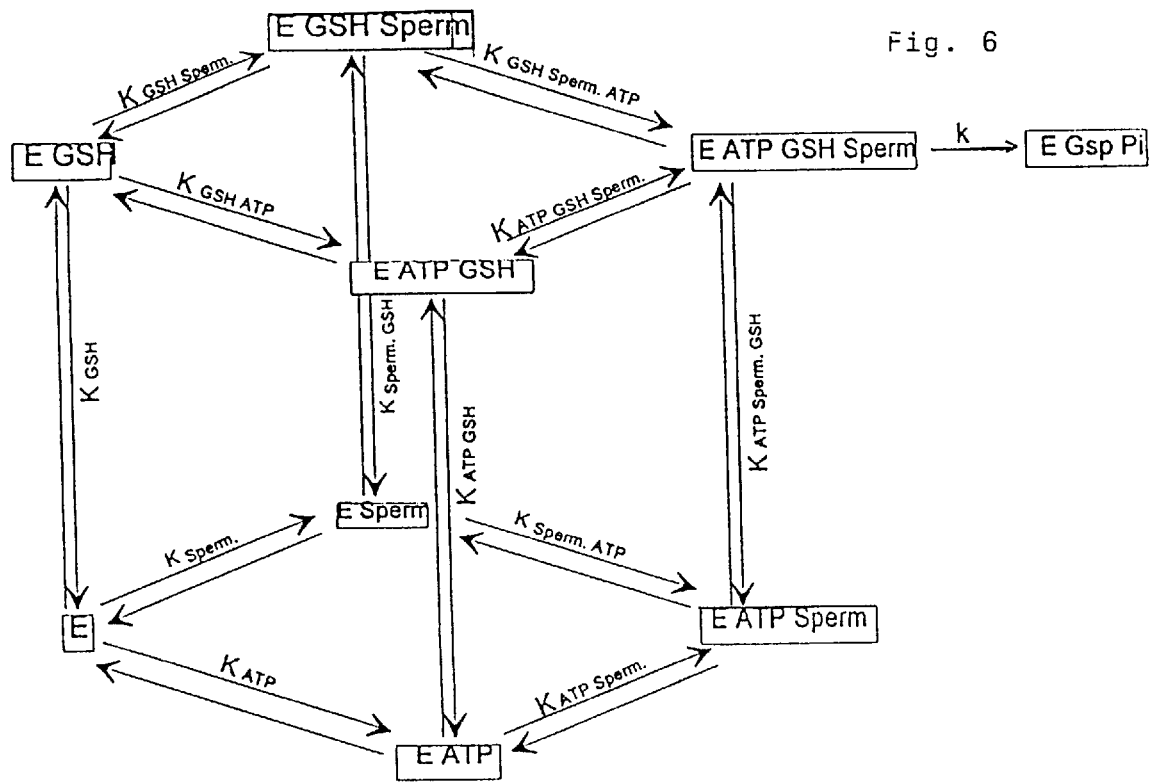

FIG. 6. Scheme of the glutathionylspermidine synthetase as a rapid equilibrium random terreactant system.

Figure 7:
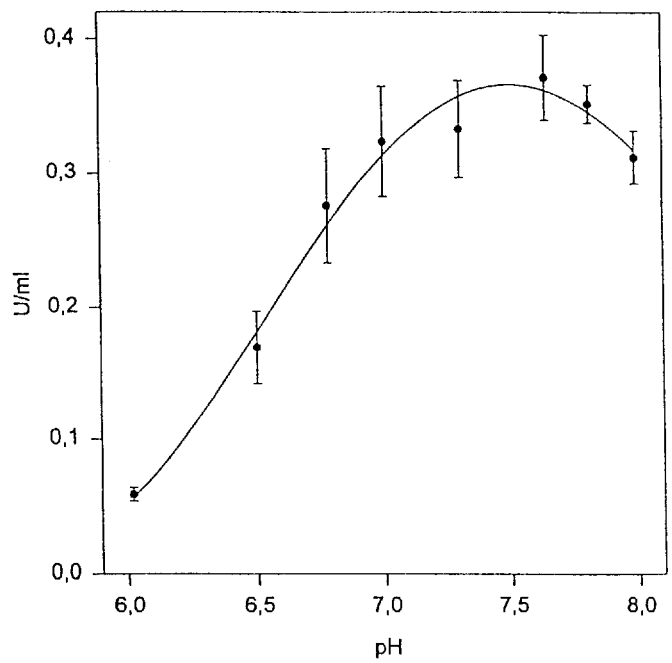

FIG. 7. pH optimum of glutathionylspermidine synthetase. Product formation of Gsp was analyzed as described under Experimental Procedures. Values are means±standard deviations from two independent measurements done at 10 and 20 min.

Figure 8:
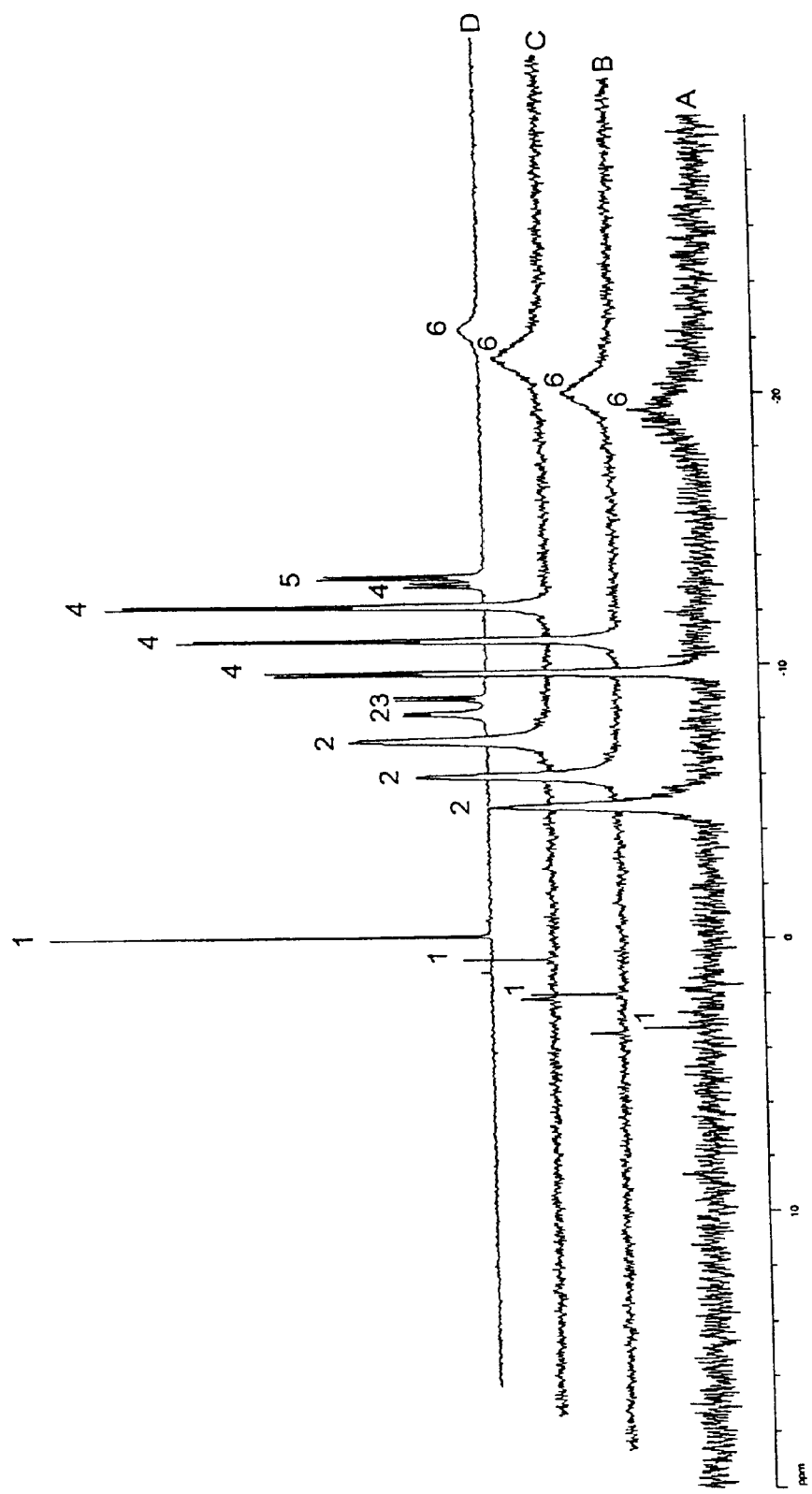

FIG. 8. $^{31}P$ NMR spectra during the reaction of the glutathionylspermidine synthetase with their substrates. (A) GspS in the presence of ATP, incubation time=0 min, scanning time=7 min; (B) GspS in the presence of ATP, incubation time=5 h, scanning time=30 min; (C) addition of the second substrate (GSH or spermidine), incubation time=5 h, scanning time=30 min; (D) addition of the third substrate (GSH or spermidine), incubation time=5 h, scanning time=30 min. The peaks are assigned to (1) inorganic phosphate, (2) ATP, γ-P, (3) ADP, β-P, (4) ADP, α-P, (5) ATP, α-P, and (6) ATP, β-P.

Figure 9B:
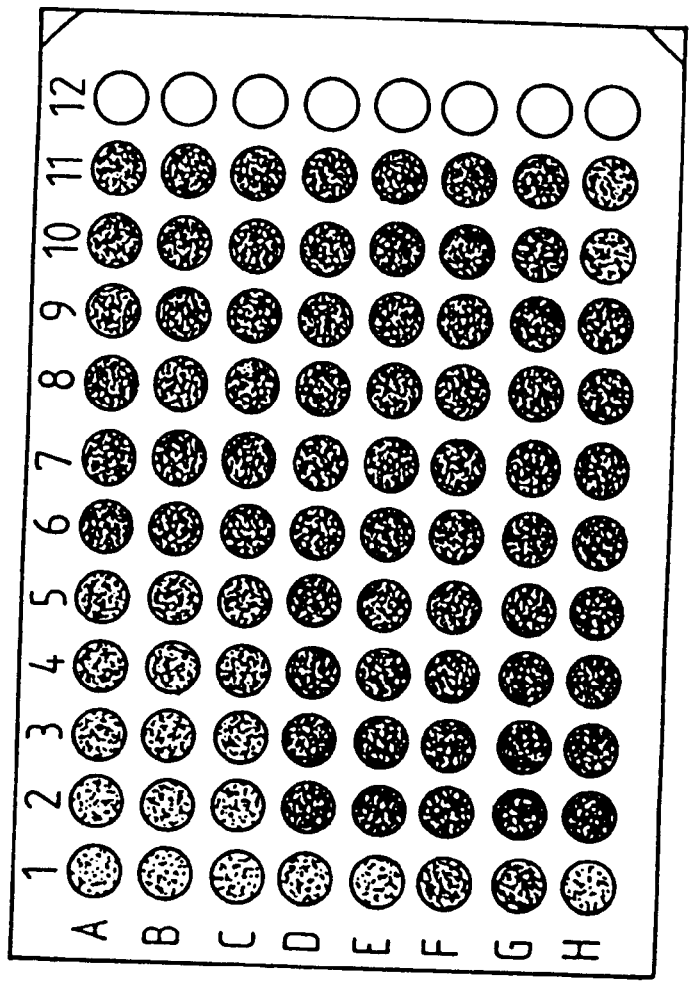

FIG. 9. Malachite green calorimetric assay for liberation of inorganic phosphate. The malachite green colorimetric assay for liberation of inorganic phosphate (1) was used for fast detection of GspS activity.

The standard assay was carried out at 25.0° C. in a volume of 0.15 ml containing 50 mM Bis-Tris-propane, 50 mM Tris, pH 7.5, 5 mM $MgSO_4$, 1 mM EDTA, 5 mM DTT, 5 mM ATP, 10 mM GSH, 10 mM spermidine, and GspS. After an incubation of 10 min the malachite green reagent was added for detection of GspS activity.

High enzymatic GspS activity is visualized by a dark green color of the assay.

Blank=standard assay with water instead of GspS; no liberation of phosphate, therefore the color of the assay is yellow instead of green.

ADP significantly inhibits GspS. The type of inhibition is competitive with respect to ATP.

Concentration of ATP (see heading) and ADP (see table).

| | | ATP | | | | | | | | | |
|---|---|---|---|---|---|---|---|---|---|---|---|
| | | 0.2 | 0.2 | 0.5 | 0.5 | 1 | 1 | 2 | 2 | 5 | 5 |
| | | | | | | [mM]:> | | | | | |
| | | mM | mM | mM | mM | mM | mM | mM | mM | mM | mM |
| 1 | 2 | 3 | 4 | 5 | 6 | 7 | 8 | 9 | 10 | 11 | 12 |
| A | blank | 10 | 10 | 10 | 10 | 10 | 10 | 10 | 10 | 10 | 10 |
| B | blank | 5 | 5 | 5 | 5 | 5 | 5 | 5 | 5 | 5 | 5 |
| C | blank | 2 | 2 | 2 | 2 | 2 | 2 | 2 | 2 | 2 | 2 |
| D | blank | 1 | 1 | 1 | 1 | 1 | 1 | 1 | 1 | 1 | 1 |
| E | | 0.5 | 0.5 | 0.5 | 0.5 | 0.5 | 0.5 | 0.5 | 0.5 | 0.5 | 0.5 |

-continued

| | 1 | mM 2 | mM 3 | mM 4 | mM 5 | mM 6 | mM 7 | mM 8 | mM 9 | mM 10 | mM 11 | 12 |
|---|---|---|---|---|---|---|---|---|---|---|---|---|
| ATP | | 0.2 | 0.2 | 0.5 | 0.5 | 1 [mM]:> | 1 | 2 | 2 | 5 | 5 | |
| F | | 0.2 | 0.2 | 0.2 | 0.2 | 0.2 | 0.2 | 0.2 | 0.2 | 0.2 | 0.2 | |
| G | | 0.1 | 0.1 | 0.1 | 0.1 | 0.1 | 0.1 | 0.1 | 0.1 | 0.1 | 0.1 | |
| H | | 0 | 0 | 0 | 0 | 0 | 0 | 0 | 0 | 0 | 0 | |

EXAMPLES

Examples 1

Purification of GspS

Production of starting material: *C. fasciculata* was grown in a medium previously described (27) in a 100-1 fermenter at 27° C. with continuous stirring (200 rpm) and aeration (0.1 vvm). Organisms were harvested in the late logarithimic growtlh phase by continuous flow centrifugation. The pellet was resuspended with 100 mM HEPES buffer (pH 7.5) containing 1 mM DTT and 1 mM $MgSO_4$. After centrifugation the cells were stored at −20° C.

GspS Assay: The assays wcrc carried out at 25.0° C. in a volume of 0.9 ml containing 50 mM Bis-Tris-propanec, 50 mM Tris, ph 7.5, 5 mM $MgSO_4$, 1 mM EDTA, 5 mM DTT, 5 mM ATP, 10 mM GSH, and 10 mM spermidine (1). The assay for TS was carried out as described by Smitih et al. (1). Aliquots were talcen after 20 min. For thiol analysis a precolumn derivatization with the fluorescent thiol-specific reagent, monobromobimane (Calbiochem), was used as described previously (2). All samples for HPLC analysis were diluted four-fold with water. Separation and analytical conditions were as described previously (28). HPLC-analysis was performed with a Jasco-HPLC-system consisting of an autosampler (851-AS), a pump (PU-980), a ternary gradient unit (LG-980-02), and a highly sensitive fluorescence detector (FP-920), which enabled a precise analysis of the small product peak in the presence of numerous other and larger ones. An external standard (0.04 mM Gsp) was used for integration calibration of the samples.

Extraction in Aqueous Two-Phase Systems: 250 g cells were suspended in 250 ml of 20 mM Bis-Tris-propane puffer, pH 7.5, disrupted by freezing in liquid nitrogen and thawing. The crude homogenate was subjected to an aqueous two-phase extraction at room temperature. All other operations were performed at 4° C.

For extraction of GspS aqueous two-phase systems (total mass 900 g) were prepared by weighing in concentrated solutions of the phase components and finally the crude extract (FIG. 3). A poly(ethylene glycol) (PEG)/phosphate system containing 7.5% (wlw) $PEG_{6000}$, 13% (w/w) Na—K-phosphate, pH 7.0, and 40% crude homogenate (or water in the blank systems) was used. The mixture was gently shaken for 10 min at room temperature and separated by centrifugation at 5000 g. The top phase was sucked off and applied to a bottom phase of a blank system. After mixing, centrifugation, and separation of the phases the PEG-rich top phase of the second phase extraction was mixed with a blank bottom phase, adjusted to pH 6.0 with HCl. This third system was mixed again, centrifuged, and separated. Now the GspS was found in the phosphate-rich bottom phase.

Diafiltration: The phosphate-rich third bottom phase and other pooled enzyme fractions were diafiltrated with an omega membrane with a cut-off of 30 kDa (Filtron Minisette) using a Pro lFlux M12 (Amicon) at 0.2 MPa and a 500-fold volume of 2 mM Bis-Tris-propane buffer, pH 8.0.

Resource Q Chromatography: A BioLogic-System (Bio-Rad) was used at 4° C. for all chromatographies. The diafiltrated protein mixture was applied onto a Resource Q column (6 ml) (Pharmacia) equilibrated with 2 mM Bis-Tris-propane buffer, pH 8.0. After washing with 10 column volumes of equilibration buffer, the bound proteins were eluted at a flow rate of 1 ml/min with a gradient of 0.0 to 0.4 M KCI (100% B) as follows: t=0 min. B=0%; t=20 min, B=15%; t=40 min, B=15%; t=60 min, B=30%; t=120 min, B=30%; t=150 min, B=100%. The GspS eluted at 0.27 M KCI and the pooled active fractions were diafiltrated with 2 mM Bis-Tris-propane buffer, pH 6.0.

Poros 20 Pi Chromatography: The diafiltrated proteins were applied onto Poros 20 Pi (0.46×10 cm, 1.7 ml) (Perseptive Bioystems) equilibrated with 2 mM Bis-Tris-propane buffer, pH 6.0. After washing with 10 column volumes of equilibration buffer, bound proteins were eluted at a flow rate of 4 ml/min with a gradient of 0 to 1 M NaCl (100% B) as follows: t=0 min, B=0%; t=8 min, B=35%; t=16 min, B=35%; t=17 min, B=37%; t=21 min, B=37%; t=25 min, B=100%. GspS eluted at 0.7 M NaCl.

Poros 20 PE Chromatography: Pooled active fractions were adjusted to 1 M ammonium sulfate and applied onto a hydrophobic interaction chromatography column Poros 20 PE (0.46×10 cm, 1.7 ml) (Perseptive Biosystems) equilibrated with 20 mM Bis-Tris-propane buffer, pH 8.0, containing 1 M ammonium sulfate, washed with 10 column volumes of equilibration buffer, and eluted with a linear gradient of 1 to 0 M ammonium sulfate and a flow rate of 4 ml/min over 7.5 min. GspS eluted at 0.75 M ammonium sulfate. Pooled active fractions were diafiltrated with 10 mM Bis-Trispropane buffer, pH 6.8.

Mono P Chromatography: The diafiltrated fraction was applied onto a Mono P HR 5/20 column (4 ml) (Pharmacia) for anion exchange chromatography. The column was equilibrated with 10 mM Bis-Tris-propane buffer, pH 6.8. After washing with 10 column volumes of equilibration buffer, bound proteins were eluted with a gradient of 0 to 1 M NaCl (100% B) as follows: t=0 min, B=0%; t=20 min, B=25%; t=40 min. B=25%; t=60 min, B=50%; t=80 min, B=50%; t=100 min, B=100%. The flow rate was 1 ml/min. GspS eluted at 0.45 M NaCl.

Results: The purification strategy outlined above resulted in a GspS preparation with a specific activity of 37.6 U/mg at an overall yield of about 20%. The purification factor achieved was 12,500. As is seen from table 1, the phase distribution system applied proved to be highly efficient in enriching GspS.

The optimized procedure was based on a factorial design of phase compositions, i.e. $PEG_{6000}$/phosphate (7.5/13%

(w/w)), PEG$_{4000}$/phosphate (8/14% (w/w)), PEG$_{1550}$/phosphate (9/18% (w/w)), each tested at pH 4.0, 5.5, and 7.0 and containing 40% cell lysate. By centrifugation the cell debris were concentrated in a gum-like interphase if the pH of the system was 5.5. A graphical evaluation of the experimental data (not shown) clearly demonstrated a significant increase in the partition coefficient of GspS with increasing pH, and a decrease in the partition coefficient of the total protein with increasing molecular weight of PEG. The best system, containing 7.5% (w/w) PEG$_{6000}$, 13% (w/w) phosphate, pH 7.0, yielded an extraction of GspS into the top phase (FIG. 3) with a purification factor of 30 in one step.

Some residual turbidity left in the top phase of the initial extraction could be eliminated by a second extraction step, mixing the primary top phase with a bottom phase of an identical blank system. By these systems a proteolytic activity, as observed with casein yellow, and an ATPase activity were quantitatively removed by extraction into the bottom phases. Simultaneously GspS was completely separated from trypanothione synthetase (TS) activity. While GspS was recovered completely in the top phase, TS activity was extracted into the bottom phase (FIG. 3), but proved to be unstable and was not purified further. After two extractions into top phases GspS was essentially free of interfering enzymatic activities and could be precisely quantitated by ATP hydrolysis in the presence of glutathione and spermidine. The final chromatographic purification of GspS, however, was impaired by the high phosphate concentration and viscosity of the top phase in which the enzyme was dissolved. GspS was therefore extracted from the second top phase into the bottom phase of a third system by lowering its pH to 6.0 without loss of activity. The GspS in the phosphate-rich bottom phase was diafiltrated and then could be loaded onto a Resource Q column. GspS thus purified appeared homogeneous by SDS-PAGE (FIG. 4) and by titration curve analysis (FIG. 5).

Example 2

Determination of Physical Parameters of GspS

Molecular mass estimation by gel permeation chromatography: Proteins were applied onto a gel permeation chromatography column Superose 12 (HR 10/30) (Pharmacia) equilibrated with 20 mM Bis-Tris-propane buffer, pH 7.5 containing 0.15 M NaCl and eluted with a flow rate of 0.3 ml/min. Blue dextran (2,000 kDa), thyroglobulin (669 kDa), ferritin (440 kDa), β-amylase (200 kDa), alcohol dehydrogenase (150 kDa), bovine serum albumin (67 kDa), and carbonic anhydrase (30 kDa) were used as standards.

Gel permeation chromatography on Superose 12 indicated a molecular mass of 79 kDa. A small activity peak eluted at about 170 kDa suggesting a slight tendency of the enzyme to dimerize. In essence, however, GspS of *C. fasciculata* was present as a monomeric enzyme of 79 kDa.

Electrophoresis: The subunit molecular weight was determined by SDS-PAGE (28) using a PhastGel Gradient 8-25 (Pharmacia) with the following molecular weight standards: phosphorylase b (94 kDa), bovine serum albumin (67 kDa), ovalbumin (43 kDa), carbonic anhydrase (30 kDa), trypsin inhibitor (20.1 kDa), and α-lactalbumin (14.4 kDa).

A subunit molecular mass of GspS of 78 kDa was estimated by SDS-PAGE.

The native molecular weight was determined by native PAGE using a PhastGel Gradient 8-25 (Pharmacia) with the same following molecular weight standards and additionally: thyroglobulin (669 kDa), ferritin (440 kDa), catalase (232 kDa), and lactate dehydrogenase (140 kDa).

A molecular weight of 78 kDa was obtained by gradient gel electrophoresis of the native enzyme. The identity of the 78 kDa band with GspS was confirmed by activity staining, i.e. phosphate liberation upon incubation with $Mg^{2+}$-ATP, GSH, and spermidine (not shown).

The isoelectric point was determined by isoelectric focusing using a PhastGel IEF 3–9 (Pharmacia) with a broad pI calibration kit and by titration curve analysis with PhastGel IEF 3–9. The latter technique is a two-dimensional electrophoresis. In the first dimension, a pH gradient is generated. The gel is then rotated clockwise 90° and the sample is applied perpendicular to the pH gradient across the middle of the gel (29).

For detection of GspS activity after isoelectric focusing the gels were cut into two pieces, one was silver stained for protein detection and the second was incubated for 15 min at room temperature in a solution of 100 mM HEPES, pH 7.0, 5 mM $MgSO_4$, 1 mM EDTA, 5 mM DTT, 10 mM GSH, 10 mM spermidine, and 2 mM ATP. After 15 min 2.5 ml of a staining solution containing malachite green, ammonium molybdate and Tween 20 (1) was added. Lanes containing active GspS showed a dark green colour after few minutes. The isoelectric point deduced from isoelectric focusing was at pH 4.6.

Example 3

Amino Acid Sequencing

SDS-PAGE of purified GspS was performed at a constant current of 20 mA in a separating gel (T=7.5%). For blotting, the proteins were transferred for 1.5 h onto a PVDF-membrane at 40 V/70 mA in a buffer containing 25 mM Tris base, 192 mM glycine, and 10% (v/v) methanol. The blot was stained with Coomassie blue. For peptide sequencing the band corresponding to a molecular mass of 78 kDa was cut out. This material was washed and digested with endoproteinase Lys-C as described before (30) and separated by reversed-phase HPLC (30). Peptide peaks were detected at 214 nm and collected manually. Aliquots of 15–30 $\mu$l were applied directly to biobrene-coated, precycled glass fibre filters of an sequencer (Applied Biosystems 470A) sequencer with standard gas-phase programs of the manufacturer.

N-terminal amino acid sequencing proved unsuccessful obviously due to a N-terminal blocking group. After proteolytic cleavage with endoproteinase Lys-C, however, a total of 11 peptides could be recovered from HPLC in a quality to allow sequencing. Out of these peptides, 7 could unambigously be aligned to the deduced GspS sequence of *E. coli* recently published by Bollinger et al. (25) (FIG. 1). GspS of *E. coli* and of *C. fascicillata* thus appeared to be phylogenetically related. But based on the limited sequence information, the sequence similarity between these enzymes, with only 40% identities, appears rather low.

Example 4

Kinetic Analysis

All kinetic experiments were carried out at 25.0° C. in a volume of 0.9 ml containing 50 mM Bis-Tris-propane, 50 mM Tris, pH 7.5, 1 mM EDTA, 5 mM DTT and variable concentrations of ATP (0.10, 0.13, 0.18, 0.28, 0.66 mM ATP), GSH (0.36, 0.47, 0.66, 1.11, 3.57 mM GSH), and spermidine (0.36, 0.47, 0.66, 1.11, 3.57 mM spermidine), respectively. The enzymatic tests for kinetic studies except the ADP inhibition studies were performed in the presence of phosphoenolpyruvate (10 mM) and pyruvate kinase (0.5 units). A fixed magnesium concentration of 5 mM and a GspS content of 0.072 mg (0.923 μM) was used. Aliquots were taken at 15 min and 30 min. GspS activity was analyzed by product determination as described in example 1.

The experimental data thus obtained classify the kinetic mechanism of GspS as an equilibrium random-order mechanism. Whether the complexation of the individual substrates occurs absolutely independently of each other or whether the binding substrates mutually affect affinities of cosubstrates, is less easily decided. The apparent $K_m$ values for the different substrates, however, are not significantly affected by the concentrations of the respective cosubstrates. Consequently, the deduced dissociation constants of the corresponding binary, ternary and quarternary complexes are very close for a given substrate and not significantly different. This would indeed imply a mutually independent random addition of substrates. But with regard to the inevitable scatter of data it can not be exluded that some route leading to the quarternary complex is slightly favoured. However, a rapid equilibrium random-order mechanism, as depicted in FIG. 6, complies best with the experimental data. Based on this assumption, the limiting $K_m$ values are defined as the dissociation constants of the quarternary complexes, numerically 0.25±0.02, 2.51±0.33, and 0.47±0.09 mM for $Mg^{2+}$-ATP, GSH, and spermidine, respectively. The rate limiting velocity constant then can be calculated to be 415±78 $min^{-1}$.

A quarternary complex mechanism implies that all three substrates must be assembled at the enzyme before a reaction can proceed. In order to check this hypothesis, we subjected the enzyme to long-term exposure with $Mg^{2+}$-ATP plus one of the additional substrates and monitored a potential partial reaction by $^{31}P$ NMR.

$^{31}P$ NMR spectra were recorded on a Bruker ARX 400 NMR spectrometer, at 162 MHz and locked to the deuterium resonance of $D_2O$, to detect potential partial reactions.

The experiments were carried out at 25.0° C. in a volume of 0.6 ml containing 50 mM Bis-Tris-propane, 50 mM Tris, pH 7.5, 5 mM $MgSO_4$, 1 mM EDTA, 5 mM DTT, in the presence of 20% $D_2O$. Spectra were recorded at the beginning of the experiment and after the addition of the substrates (5 mM ATP, 10 mM GSH, and 10 mM spermidine).

FIG. 8 demonstrates that with all combinations of substrates no ATP turnover could be observed within 5 hours unless the third substrate was added. These findings strongly support the assumption of a quarternary complex mechanism and explain the absence of any ATPase activity of GspS. Neither can the presumed catalytic intermediate glutathionylphosphate be formed in any detectable amount by an incomplete catalytic complex.

As already mentioned ADP significantly inhibits GspS which renders it difficult to measure GspS activity in the absence of an ATP regenerating system. The type of inhibition is competitive with respect to ATP. A $K_i$ of 80 μM was calculated which is in the range of physiological ADP concentrations. GspS also proved to be feed-back inhibited by TSH with a $K_i$ of 480 μM, which is competed by GSH.

Example 5 pH-optimum of GspS

The activity of GspS was measured essentially as described in example 4 but at pH values ranging from 6–8. GspS shows a flat pH optimum near pH 7.5 (FIG. 7).

Example 6

Use of Malachite Green Calorimetric Assay for Liberation of Inorganic Phosphate in GspS Preparations Partially Purified According to Example 1

The liberation of inorganic phosphate from ATP can be easily visualized by malachite green (FIG. 9). The test is amply used to monitor ATP hydrolyzing activities and is correspondingly unspecific. Surprisingly, the GspS preparation after aqueous two phase extraction, as described in example 1, proved to be free of any significant spontaneous ATP-hydrolyzing activity. This finding enabled us to use this fast and convenient test to measure specifically GspS activity which is accompanied by release of inorganic phosphate from ATP in the presence of glutathione, spermidine, and magnesium ions. The test can be easily adapted to mass screening as outlined below.

The malachite green calorimetric assay for liberation of inorganic phosphate (1) was used for fast detection of GspS activity during purification after column chromatography and for GspS localization on gels.

The disclosure comprises also that of EP 96 120 014.4 filed Dec. 12, 1996, the entire disclosure of which is incorporated herein by reference.

REFERENCES

1. Smith, K., Nadeau, K., Bradley, M., Walsh, C., and Fairlamb, A. H. (1992) *Protein science* 1, 874–883.
2. Shim, H. and Fairlamb, A. H. (1988) *J. Gen. Microbiol.* 134, 807–817.
3. Fairlamb, A. H., Blackburn, P., Ulrich, P., Chait, B. T., and Cerami, A. (1985) *Science* 227, 1485–1487.
4. Fairlamb, A. H. and Cerami, A. (1985) *Mol. Biochemn. Parasitol.* 14, 187–198.
5. Krauth-Siegl, R. L. and Schöneck, R. (1995) *FASEB J.* 9, 1138–1146.
6. Fairlamb, A. H. (1996) *The Biochemist* Feb/Mar, 11–16.
7. Penketh, P. G. and Klein, R. A. (1986) *Mol. Biochem. Parasitol.* 20, 111–121.
8. Penketh, P. G., Kennedy, W. P. K., Patton, C. L., and Sartorelli, A. C. (1987) *FEBS Lett.* 2, 427–431.
9. Henderson, G. B., Fairlamb, A. H., and Cerami, A. (1987) *Mol. Biochenm. Parasitol.* 24, 39–45.
10. Carnieri, E. G. S., Moreno, S. N. J., and Docampo, R. (1993) *Mol. Biochem. Parasitol.* 61, 79–86.
11. Boveris, A., Sies, H., Martino, E. E., Docampo, R., Turrens, J. F., and Stoppani, A. O. M. (1980) *Biochem. J.* 188, 643–648.
12. Babior, B. M., Kipnes, R. S., and Curnutte, J. T. (1973) *J. Clin. Invest.* 52, 741–744.
13. Klebanoff, S. J. and Rosen, H. (1979) in *Oxygen free radicals and tissue damage*, pp. 263–284, Ciba Foundation Symposia 65 Exepta Medica, Amsterdam-Oxford-New York.
14. Kraut-Siegel, R. L. and Schöneck, R. (1995) *FASEB J.* 9, 1138–1146.
15. Bailey, S., Smith, K., Fairlamb, A. H., and Hunter, W. N. (1993) *Eur. J. Biochem.* 213, 67–75.
16. Flohé, L. (1989) in *Glutathione: chemical, biochemical, and medical aspects* (Dolphin, D., Poulson. R., and Avramovic, A., eds.), pp. 643–731, John Wiley & Sons, New York.
17. Ursini, F., Maiorino, M., Brigelius-Flohé, R., Aumann, K. D., Roveri, A., Schomburg, D., and Flohé, L. (1995) *Methods Enzymol.* 252, 38–53.

18. Chance, B., Sies, H., and Boveris, A. (1979) *Physiol. Rev.* 59, 527–605.
19. Flohé, L., Giertz, H., and Beckmann, R. (1985) in *Handbook of inflammation* (Bonta, L., Bray, M. A., and Parnham, M. J., eds.), pp. 255–281, Elsevier Science Publishers B.V., Amsterdam.
20. Tabor. H. and Tabor, C. W. (1975) *J. Biol. Chem.* 250, 2648–2654.
21. Smith, K., Borgas, A., Ariyanayagam, M. R., and Fairlamb, A. H. (1995) *Biochem. J.* 312, 465–469.
22. Henderson, G. B., Yamaguchi, M., Novoa, L., Fairlamb, A. H., and Cerami, A. (1990) *Biochemistry* 29, 3924–3929.
23. Nogoceke, E., D. U. Gommel, M. Kiess, H. M. Kalisz, and Flohé, L. (1997) *Biol. Chem.* 378, 827–836.
24. Gommel, D. U., E. Nogoceke, M. Morr, M. Kiess, H. M. Kalisz, and Flohé, L. (1997) *Eur. J. Biochem.* 248, 913–918.
25. Bollinger, J. M., Kwon, D. S., Huisman, G. W., Kolter, R., and Walsh, C. T. (1995) *J. Biol. Chem.* 270, 14031–14041.
26. Kwon, D. S., Lin, C.-H., Chen, S., Coward, J. K., Walsh, C. T., and Bollinger, J. M. (1997) *J. Biol. Chem.* 272, 2429–2436.
27. Le Trant, N., Meshnick, S. R., Kitchener, K., Eaton, J. W., and Cerami, A. (1983) *J. Biol. Chem.* 258, 125–130.
28. Fairlamb, A. H., Henderson, G. B., Bacchi, C. J., and Cerami, A. (1987) *Mol. Biochem. Parasitol.* 24, 185–191.
29. Rosengreen, A., Bjellquist, B., & Gasparic, V. (1977) in *Electrofocusing and isotachophoresis* (Radola, B. J. & Graesslin, D., eds.), pp. 165–171, W. de Gruyter, Berlin.
30. Maiorino, M., Roche, C., Kieβ, M., Koenig, K., Gawlik, D., Matthes, M., Naldini, E., Pierce, R., and Flohé, L. (1996) *Eur. J. Biochem.* 238, 838–844.

We claim:

1. An isolated protein catalyzing the synthesis of glutathionylspemidine having a pH optimum of said synthesis of about pH 7.5 and having a molecular weight of 78,000±3,000 Da by SDS-polyacrylamide gel electrophoresis.

2. An isolated protein catalyzing, the synthesis of glutathionylspermadine comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SED ID NO: 8, wherein said potein has a pH optimum of said synthesis of about pH 7.5.

3. A protein according to claim 1 isolated from a species of the family of trypanosomatids (Trypanosomatidae).

4. A protein according to claim 3 wherein said species is selected from the group consisting of Trypanosoma sp., Leishmania sp., Herpetomonas sp., Leptomonas sp., Blastocrithidia sp., Crithidia sp., and Phytomonas sp.

5. A protein according to claim 4 wherein said species is C. fasciculata.

6. A protein according, to claim 2 produced by the method comprising the steps of:
    (a) culturing a host cell transformed with a nucleic acid selected from the group consisting of ncleic acids encoding any one of the amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, and,
    (b) isolating said protein from said host cell or its growth medium.

7. A protein according to claim 1 or 2 comprising a partial deduced amino acid sequence selected from the group consisting of SEQ ID NO: 8, and sequences homologous to said SEQ ID NO: 8 having the same number of amino acids as SEQ ID NO: 8 and being identical to SEQ ID NO: 8 in more than 70% of the amino acid residues.

8. A protein according to claim 7 wherein said sequence is identical to SEQ ID NO: 8 in more than 75% of the amino acid residues.

9. A protein according to claim 1 or 2 encoded in part by a partial DNA sequence selected from the group consisting of a partial DNA sequence of SEQ ID NO: 9 and any other DNA sequences having the same number of nucleotides and being identical to SEQ ID NO: 9 in more than 70% of the nucleotides.

10. A protein accordingu to claim 9 wherein said other DNA sequence is identical to SEQ ID NO: 9 in more than 75% of the nucleotides.

11. A protein according to claim 9 wherein the complementary strand of said other DNA sequence hybridizes to SEQ ID NO: 9 at a temperature of at least 25° C. and at a NaCl concentration of 1M.

\* \* \* \* \*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:1:

Val Pro Phe Gly Glu Val Gln Gly Tyr Ala Pro Gly His Ile Pro Ala
1            5                    10                15

Tyr Ser Asn Lys
        20

(2) INFORMATION FOR SEQ ID NO:2:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:2:

Ser Ile Ile Thr Gly Leu Asp Ser Pro Phe Ala Ala Ile
1            5                    10

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

Thr Tyr Glu Pro Thr Glu
1           5

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:4:

Asn Glu Ile Pro Arg Pro Leu Thr His Lys
1           5                 10

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:5:

Leu Asp Leu Asn Asp Pro Ala Glu
1           5

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:6:

Ile Leu Pro Ile Ile Tyr His Asn His Pro Asp His Pro Ala Ile Leu
1               5                  10                  15

Arg Ala Glu (2) INFORMATION FOR SEQ ID NO:7:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:7:

Ile Val Gly Arg Val Gly Arg Asn Val Thr Ile Thr Asp Gly
1               5                  10

(2) INFORMATION FOR SEQ ID NO:8:

(i) SEQUENCE CHARACTERISTICS:
            (A) LENGTH: 573 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (ix) FEATURE:
            (A) NAME/KEY: Modified-site
            (B) LOCATION: 191
            (D) OTHER INFORMATION: /note= "Xaa = Lys or Asn"

(ix) FEATURE:
            (A) NAME/KEY: Modified-site
            (B) LOCATION: 463
            (D) OTHER INFORMATION: /note= "Xaa = Val or Asp"

(ix) FEATURE:
            (A) NAME/KEY: Modified-site
            (B) LOCATION: 479
            (D) OTHER INFORMATION: /note= "Xaa = Val or Gly"

(xi) SEQUENCE DESCRIPTION: SEQ ID NO:8:

Tyr Ser Asn Lys His Asp His Phe Phe Ser Gly Glu Arg Ser Ile Asp
1               5                  10                  15

Asp Asn Val Phe Cys Gly Phe Lys Tyr Gln Cys Val Glu Phe Ala Arg
                20                  25                  30

Arg Trp Leu Leu Glu Arg Lys Gly Leu Val Leu Pro Asp Val Asn Trp
            35                  40                  45

Ala Cys His Ile Phe Lys Leu Lys Ser Val Lys Asp Ala Ala Thr Ala
        50                  55                  60

Glu Glu Val Pro Val Ile Ala Val Arg Asn Gly Thr Glu Ala Lys Pro
65                  70                  75                  80

-continued

```
Glu Pro Asp Thr Leu Ile Ile Tyr Pro Ser Ser Asp Val Asn Thr Val
                85                  90                  95

Gly His Val Gly Ala Ile Thr Glu Val Gly Asp Tyr Val Cys Ile
            100                 105                 110

Ala Asp Gln Asn Tyr Arg Phe His Lys Trp Glu Ala Ser Tyr Ser Tyr
            115                 120                 125

Lys Leu Lys Leu Gln His Lys Asp Gly Val Trp Thr Ile Ile Asp Asp
130                 135                 140

Ile Asp Pro Asn Asp Val Glu Ile Pro Leu Gly Trp Val Thr Phe Pro
145                 150                 155                 160

Gly Tyr Glu Asn Arg Pro Glu Gly Ala Ala Pro Pro Ala Leu His Pro
                165                 170                 175

Ser Leu His Phe Gln Pro Pro Glu Glu Pro Tyr Leu Val Arg Xaa Thr
            180                 185                 190

Tyr Glu Pro Thr Glu Thr Lys Ala Asn Trp Leu Asp Leu Asn Asp Pro
            195                 200                 205

Ala Glu Lys Leu Phe Val Glu Glu Phe Gly Met Asp Val Ser Arg Ser
210                 215                 220

Arg Leu Glu Glu Thr Thr Val Asn Tyr Tyr Glu Cys Asp His Glu Phe
225                 230                 235                 240

His Leu Arg Cys Ile Ala Tyr Gly Thr Gln Leu His Asp Tyr Phe Met
            245                 250                 255

Glu Ala Thr Ala Gln Val Ile Asn Asp Glu Arg Leu Arg Ile Phe Lys
            260                 265                 270

Ile Pro Glu Glu Leu Trp Pro Arg Met Arg His Ser Trp Lys Tyr Gln
            275                 280                 285

Gln Thr Tyr Ile Ser Gly Arg Phe Asp Phe Ala Tyr Asn Asn Glu Thr
            290                 295                 300

His Gln Met Lys Cys Phe Glu Tyr Asn Ala Asp Ser Ala Ser Thr Leu
305                 310                 315                 320

Leu Glu Cys Gly Arg Ile Gln Gln Lys Trp Ala Glu Ser Ala Gly Leu
                325                 330                 335

Asp Lys Glu Gly Thr Arg Gly Ser Gly Trp Ala Val Glu Arg Asn Leu
            340                 345                 350

Pro Thr Ala Trp Ala Thr Cys Gly Ala Thr Gly Arg Val His Phe Leu
            355                 360                 365

Val Asp Asp Glu Lys Glu Gln Tyr Thr Ala Leu Tyr Cys Leu Gln
370                 375                 380

Ala Arg Lys Arg Gly Leu Glu Gly Lys Leu Cys Val Met Tyr Asp Glu
385                 390                 395                 400

Phe Arg Phe Asn Glu Glu Gly Tyr Val Val Asp Ser Asp Gly Val Arg
                405                 410                 415

Val Arg Asn Ile Trp Lys Thr Trp Met Trp Glu Ser Ala Ile Ser Asp
            420                 425                 430

Tyr Phe Ala Ala Gln Ala Glu Arg Val Arg Leu Glu Gly Asp Ala Ala
            435                 440                 445

Asp Lys Val Arg Leu Cys Asp Leu Met Leu Gly Lys Asp Trp Xaa Ile
            450                 455                 460

Leu Tyr Phe Glu Pro Met Trp Lys Leu Ile Pro Ser Asn Lys Xaa Ile
465                 470                 475                 480

Leu Pro Ile Ile Tyr His Asn His Pro Asp His Pro Ala Ile Leu Arg
                485                 490                 495
```

```
Ala Glu Tyr Glu Leu Thr Asp Glu Leu Leu Arg Cys Gly Tyr Ala Arg
            500                 505                 510

Lys Pro Ile Val Cys Arg Val Gly Arg Asn Val Thr Ile Thr Asp Gly
        515                 520                 525

Thr Gly Glu Val His Ala Glu Ser Gly Gly Asn Phe Gly Glu Arg Asp
    530                 535                 540

Met Ile Tyr Gln Glu Leu Phe Ser Leu Thr Lys Gln Asp Gly Tyr Tyr
545                 550                 555                 560

Ala Ile Ile Gly Gly Met Leu Gly Asp Ala Phe Ser Gly
                565                 570
```

(2) INFORMATION FOR SEQ ID NO:9:

(i) SEQUENCE CHARACTERISTICS:
        (A) LENGTH: 1719 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 483
        (D) OTHER INFORMATION: /note= "M = C or A"

(ix) FEATURE:
        (A) NAME/KEY: misc_feature
        (B) LOCATION: 489
        (D) OTHER INFORMATION: /note= "R = G or A"

(ix) FEATURE:
        (A) NAME/KEY: misc_feature
        (B) LOCATION: 546
        (D) OTHER INFORMATION: /note= "S = C or G"

(ix) FEATURE:
        (A) NAME/KEY: misc_feature
        (B) LOCATION: 555
        (D) OTHER INFORMATION: /note= "R = G or A"

(ix) FEATURE:
        (A) NAME/KEY: misc_feature
        (B) LOCATION: 573
        (D) OTHER INFORMATION: /note= "K = G or T"

(ix) FEATURE:
        (A) NAME/KEY: misc_feature
        (B) LOCATION: 624
        (D) OTHER INFORMATION: /note= "Y = C or T"

(ix) FEATURE:
        (A) NAME/KEY: misc_feature
        (B) LOCATION: 627
        (D) OTHER INFORMATION: /note= "W = A or T"

(ix) FEATURE:
        (A) NAME/KEY: misc_feature
        (B) LOCATION: 687
        (D) OTHER INFORMATION: /note= "S = G or C"

(ix) FEATURE:
        (A) NAME/KEY: misc_feature
        (B) LOCATION: 933
        (D) OTHER INFORMATION: /note= "R = G or A"

(ix) FEATURE:
        (A) NAME/KEY: misc_feature
        (B) LOCATION: 954
        (D) OTHER INFORMATION: /note= "R = G or A"

(ix) FEATURE:
  (A) NAME/KEY: misc_feature
  (B) LOCATION: 966
  (D) OTHER INFORMATION: /note= "R = G or A"

(ix) FEATURE:
  (A) NAME/KEY: misc_feature
  (B) LOCATION: 981
  (D) OTHER INFORMATION: /note= "S = G or C"

(ix) FEATURE:
  (A) NAME/KEY: misc_feature
  (B) LOCATION: 984
  (D) OTHER INFORMATION: /note= "R = G or A"

(ix) FEATURE:
  (A) NAME/KEY: misc_feature
  (B) LOCATION: 1388
  (D) OTHER INFORMATION: /note= "W = T or A"

(ix) FEATURE:
  (A) NAME/KEY: misc_feature
  (B) LOCATION: 1436
  (D) OTHER INFORMATION: /note= "K = T or G"

(xi) SEQUENCE DESCRIPTION: SEQ ID NO:9:

```
TACAGCAACA AGCACGATCA CTTCTTCTCG GGTGAGCGCA GCATTGACGA TAACGTCTTC      60
TGCGGCTTCA AGTACCAGTG CGTCGAGTTC GCGCGCCGCT GGCTGTTGGA GCGGAAGGGG     120
CTGGTGCTGC CGGACGTGAA TTGGGCGTGC CACATCTTCA AGCTCAAGAG CGTGAAGGAT     180
GCCGCGACGG CGGAGGAGGT GCCGGTGATC GCCGTGCGCA ACGGCACGGA GGCGAAGCCG     240
GAGCCCGACA CGCTGATCAT CTACCCCTCG TCGGACGTCA ACACCGTGGG CCACGTCGGC     300
GCCATCACGG AGGTCGGCGA CGACTACGTG TGCATTGCGG ACCAGAACTA CCGCTTTCAC     360
AAGTGGGAGG CGTCCTACTC CTACAAGTTG AAGCTGCAGC ACAAGGATGG GGTTTGGACG     420
ATCATCGACG ACATCGACCC CAACGATGTC GAGATTCCGC TTGGCTGGGT GACCTTCCCC     480
GGMTACGARA ACCGGCCGGA AGGCGCCGCG CCACCGGCGC TGCACCCCTC TCTCCACTTC     540
CAGCCSCCGG AGGARCCGTA CCTGGTCCGC AAKACGTACG AGCCGACGGA GACGAAGGCG     600
AACTGGCTGG ATTTGAACGA CCCYGCWGAG AAGCTCTTTG TGGAGGAGTT CGGCATGGAC     660
GTCAGCCGCT CCCGCCTCGA GGAGACSACG GTGAACTACT ACGAGTGCGA CCATGAGTTC     720
CACCTCCGCT GCATCGCCTA CGGGACGCAG CTGCACGACT ACTTCATGGA GGCCACCGCG     780
CAGGTCATCA ACGACGAGCG GCTCCGCATC TTTAAGATTC CAGAGGAGCT GTGGCCCCGC     840
ATGCGCCACT CCTGGAAGTA CCAGCAGACG TACATCTCTG GCCGCTTTGA CTTCGCCTAC     900
AACAACGAGA CGCACCAGAT GAAGTGCTTC GARTACAACG CCGACAGCGC GTCRACGCTG     960
CTGGARTGCG GCCGCATTCA SCARAAGTGG GCCGAGTCGG CGGGGCTGGA CAAGGAGGGC    1020
ACGCGCGGCT CCGGCTGGGC CGTCGAGCGC AACCTGCCGA CCGCGTGGGC CACCTGCGGC    1080
GCCACTGGTC GCGTGCACTT CCTCGTGGAC GATGAGAAGG AGGAGCAGTA CACGGCCCTT    1140
TACTGCCTGC AGGCGCGGAA GCGTGGGCTG GAGGGGAAGC TGTGCGTCAT GTACGACGAG    1200
TTCCGCTTCA ACGAGGAGGG CTACGTCGTG GACAGCGATG GGGTGCGGGT GCGCAACATT    1260
TGGAAGACGT GGATGTGGGA GTCGGCCATC AGCGACTACT TCGCCGCGCA GGCCGAGCGC    1320
GTGCGACTGG AAGGCGACGC CGCCGACAAG GTGCGGCTCT GTGACCTGAT GCTCGGCAAG    1380
GACTGGGWCA TCTTGTACTT TGAGCCGATG TGGAAGCTGA TCCCGAGCAA CAAGGKCATC    1440
CTGCCCATCA TCTACCACAA CCACCCTGAT CACCGGCGCA TCCTGCGCGC TGAGTACGAG    1500
CTCACCGACG AGCTCCTACG CTGTGGCTAC GCCAGGAAGC CGATTGTTTG CCGTGTCGGC    1560
```

-continued

| | | | | |
|---|---|---|---|---|
| CGCAACGTCA | CCATCACCGA | CGGCACGGGT | GAGGTGCACG | CCGAGTCGGG CGGCAACTTC | 1620 |
| GGCGAGCGGG | ATATGATTTA | CCAGGAGCTC | TTCTCCCTGA | CGAAGCAGGA TGGTTATTAC | 1680 |
| GCGATCATCG | GCGGCATGCT | GGGCGACGCG | TTCAGCGGC | | 1719 |